United States Patent [19]

Neary

[11] 4,285,697
[45] Aug. 25, 1981

[54] FOOD SPOILAGE INDICATOR

[76] Inventor: Michael P. Neary, Apt. 934, 825 Calle Mejia, Santa Fe, N. Mex. 87501

[21] Appl. No.: 945,881

[22] Filed: Sep. 26, 1978

[51] Int. Cl.³ .................... G01N 33/02; G01N 31/22; C09K 3/34
[52] U.S. Cl. .................. 23/230 LC; 23/232 R; 252/299.7; 252/408; 422/57; 422/58; 422/86; 422/87; 426/87; 428/1
[58] Field of Search ........... 23/230 LC; 252/408 LC, 252/299; 116/206; 428/1; 422/83, 57; 426/87

[56] References Cited

U.S. PATENT DOCUMENTS

| 2,485,566 | 10/1940 | Clark | 116/206 X |
|---|---|---|---|
| 3,067,015 | 12/1962 | Lawdermilt | 426/87 X |
| 3,585,381 | 6/1971 | Hodson | 428/1 X |
| 3,927,977 | 12/1975 | Jacobs | 422/83 X |
| 4,003,709 | 1/1977 | Eaton | 426/87 X |
| 4,040,749 | 8/1977 | David | 23/230 LC X |
| 4,048,358 | 9/1977 | Shanks | 23/230 LC X |
| 4,161,557 | 7/1979 | Suzuki | 252/299 X |

Primary Examiner—Sidney Marantz
Attorney, Agent, or Firm—Thos. A. Wilson

[57] ABSTRACT

A food spoilage indicator comprising a liquid crystal disposed in a carrier of plastic tape, at least one portion of which is semi-permeable to gases generated in food spoilage.

3 Claims, No Drawings

FOOD SPOILAGE INDICATOR

Every year thousands of people consume spoiled canned food without knowing it. The result is illness and sometimes death. If it was possible to determine the extent of spoilage of canned foods prior to consumption much human misery could be relieved.

An object of the present invention is to provide means for detecting spoilage in canned food. Other objects will be appreciated from the following description of the invention.

The invention to be described relates to the above problem and is a food spoilage indicator. The invention depends on the discovery that: (1) the appearance or color of a liquid crystal can be significantly altered by absorbed gas and/or (2) that liquid crystals can form micelles which can contain chemical indicators.

It is almost always the case that when organic matter such as food is innoculated with bacteria or fungus or yeast and they start to multiply the process of decay is said to have started. Likewise it is always the case with bacterial or fungal or yeast initiated decay gas is evolved along with the toxins and other nitrogeneous compounds that cause food poisoning. The gases formed include: ammonia, hydrogen and carbon dioxide. Various organic acids may also be formed as well as nitrites which are usually intermediate. The rate at which these gases and/or other compounds are formed depends on the population of innoculant because they are products of metabolism. Likewise the toxins and other compounds that cause illness are also metabolic products. Thus it is clear that if the gases and other benign compounds are formed in concert with those compounds that cause illness, then a measure of the former is indicative of the latter.

Therefore the subject invention may take the following form: a small amount of liquid crystal (i.e. 5 mm $\times$ 5 mm $\times$ 0.05 mm for example) is deposited on the surface of a semi-permeable membrane. The surface thus formed is then covered with another piece of semi-permeable membrane and the perimeter or edges sealed. The spoilage indicator is now complete and ready to be inserted into the food container prior to sealing it. If the food container holds an unacceptable level of bacteria, fungi or yeast, and the food presents an acceptable medium for growth, then the metabolic products mentioned above will be produced. Further if the porosity of the semi-permeable membrane is selected to pass only molecules whose size corresponds to the gas or gases or ions of interest and if the liquid crystal or admixture of liquid crystals or admixture of liquid crystals plus indicator (or reactant) is selected for its sensitivity to metabolic product of interest, then the liquid crystal or admixture of liquid crystals or admixture of liquid crystals plus indicator will change in appearance in proportion to the quantity produced of the metabolic product of interest passing through the semi-permeable membrane into the liquid crystal.

The type of semi-permeable membranes available for use in this application are too numerous to list completely; however, protein or cellulose or carbohydrate semi-permeable membranes would be the most desirable because of the chemical commonality that they share with the food with which they come in direct contact.

Certain liquid crystal cholesteric compositions may be formulated to provide significant color change when a phase transition from the cholesteric mesomeric phase to the liquid phase occurs. Further, certain of the above formulations when caused to pass from one phase to another exhibit persistence in the final phase for up to 30 minutes even in the absences of the cause! . Typically the liquid phase of a liquid crystal is colorless and the cholesteric or mesomeric phase has bright visible colors. It is often the case that other organic chemicals can be dissolved in a liquid crystal without disturbing the typical behavior of the liquid crystal as long as the material added does not crystalize within the temperature range of contemplated use. This feature is useful in that indicators (organic chemicals) can be dissolved in the liquid crystal formulation and micellar solutions result.

Liquid crystal admixtures to accomplish the task described may include but are not limited to: cholesteryl or cholestanyl chloride, cholesteryl or cholestanyl bromide, cholesteryl or cholestanyl erucate, cholesteryl or cholestanyl olelyl carbonate, cholesteryl or cholestanyl erucyl carbonate, and cholesteryl or cholestanyl oleate.

It will be appreciated that many variations can be made without departing from the spirit of the invention so that I intend to be limited only by the following Patent Claims:

I claim:

1. In a food package, a food spoilage indicator comprising a liquid crystal disposed in a carrier of plastic tape, at least one portion of which is semi-permeable to gases generated in food spoilage, said liquid crystal being selected from the group consisting of cholesteryl or cholestanyl chloride, cholesteryl or cholestanyl bromide, cholesteryl or cholestanyl erucate, cholesteryl or cholestanyl olelyl carbonate, cholesteryl or cholestanyl erucyl carbonate, and cholesteryl or cholestanyl oleate.

2. A food package comprising food and a food spoilage indicator disposed therein in contact with said food, said food spoilage indicator consisting essentially of liquid crystals disposed in a carrier of plastic film, at least one portion of which is semi-permeable to gases of the type generated in food spoilage, said liquid crystals being selected from the group consisting of cholesteryl or cholestanyl chloride, cholesteryl or cholestanyl bromide, cholesteryl or cholestanyl erucate, cholesteryl or cholestanyl olelyl carbonate, cholesteryl or cholestanyl erucyl carbonate, and cholesteryl or cholestanyl oleate.

3. The process of indicating food spoilage which comprises disposing in intimate contact with food, a food spoilage indicator comprising a liquid crystal in a carrier of tape semi-permeable of food spoilage gases, said liquid crystal being selected from the group consisting of cholesteryl or cholestanyl chloride, cholesteryl or cholestanyl bromide, cholesteryl or cholestanyl erucate, cholesteryl or cholestanyl olelyl carbonate, cholesteryl or cholestanyl erucyl carbonate, and cholesteryl or cholestanyl oleate.

* * * * *